United States Patent
O'Neill

(10) Patent No.: US 9,778,150 B2
(45) Date of Patent: Oct. 3, 2017

(54) DYNAMIC METHOD OF OBTAINING A SAMPLE OF MATERIALS

(71) Applicant: United Technologies Corporation, Hartford, CT (US)

(72) Inventor: Christopher F. O'Neill, Hebron, CT (US)

(73) Assignee: United Technologies Corporation, Farmington, CT (US)

(*) Notice: Subject to any disclaimer, the term of this patent is extended or adjusted under 35 U.S.C. 154(b) by 47 days.

(21) Appl. No.: 14/781,836

(22) PCT Filed: Mar. 21, 2014

(86) PCT No.: PCT/US2014/031404
§ 371 (c)(1),
(2) Date: Oct. 1, 2015

(87) PCT Pub. No.: WO2014/165334
PCT Pub. Date: Oct. 9, 2014

(65) Prior Publication Data
US 2016/0054205 A1    Feb. 25, 2016

Related U.S. Application Data

(60) Provisional application No. 61/807,883, filed on Apr. 3, 2013.

(51) Int. Cl.
*G01N 1/20* (2006.01)
*G01N 1/28* (2006.01)
(Continued)

(52) U.S. Cl.
CPC .............. *G01N 1/28* (2013.01); *B22F 3/1055* (2013.01); *G01N 1/286* (2013.01); *G01N 3/22* (2013.01);
(Continued)

(58) Field of Classification Search
CPC . G01N 1/28; G01N 1/286; G01N 3/22; B22F 3/1055
(Continued)

(56) References Cited

U.S. PATENT DOCUMENTS 3,625,571 A    12/1971    Kimm
4,936,461 A    6/1990    Makiej, Jr.
(Continued)

FOREIGN PATENT DOCUMENTS

JP    2003521340 A    7/2003

OTHER PUBLICATIONS

International Search Report and Written Opinion from PCT Application Serial No. PCT/US2014/031404, dated Jul. 18, 2014, 12 pages.

*Primary Examiner* — Lisa Caputo
*Assistant Examiner* — Octavia Hollington
(74) *Attorney, Agent, or Firm* — Kinney & Lange, P.A.

(57) ABSTRACT

A method of obtaining a sample of materials includes building a product through an additive manufacturing process. A capsule is formed with an internal chamber inside of the capsule. The capsule is formed during the building of the additive manufacturing product. A sample of powder is encapsulated inside the internal chamber as the capsule is built. The internal chamber is hermetically sealed from an exterior environment to retain the sample of powder in the internal chamber.

20 Claims, 3 Drawing Sheets

(51) Int. Cl.
*G01N 3/22* (2006.01)
*B22F 3/105* (2006.01)
*B33Y 10/00* (2015.01)
*B33Y 40/00* (2015.01)

(52) U.S. Cl.
CPC ............... *B33Y 10/00* (2014.12); *B33Y 40/00* (2014.12); *G01N 2203/0284* (2013.01); *G01N 2203/0298* (2013.01)

(58) Field of Classification Search
USPC .................................................. 73/836, 863
See application file for complete search history.

(56) References Cited

U.S. PATENT DOCUMENTS

| | | | |
|---|---|---|---|
| 5,562,918 A | 10/1996 | Stimpson | |
| 5,816,404 A | 10/1998 | Seidler | |
| 6,135,771 A | 10/2000 | Dragan et al. | |
| 6,503,084 B2 | 1/2003 | Evers et al. | |
| 6,668,827 B2 | 12/2003 | Schuler et al. | |
| 7,713,518 B2 | 5/2010 | Rand | |
| 7,814,905 B2 | 10/2010 | Schuler et al. | |
| 8,342,176 B2* | 1/2013 | Jones | A61K 9/4808 128/203.15 |
| 8,828,411 B2* | 9/2014 | Yoo | A61K 9/2072 424/400 |
| 2007/0259010 A1 | 11/2007 | Yoo et al. | |
| 2010/0028897 A1 | 2/2010 | Okamoto | |
| 2012/0018926 A1 | 1/2012 | Mannella et al. | |
| 2017/0021423 A1* | 1/2017 | Berglund | F01L 3/00 |
| 2017/0157857 A1* | 6/2017 | Butcher | B29C 67/0088 |

\* cited by examiner

DYNAMIC METHOD OF OBTAINING A SAMPLE OF MATERIALS

BACKGROUND

This invention relates generally to the field of additive manufacturing. In particular, the present invention relates to the feed material used to create additively manufactured articles.

Additive manufacturing is an established but growing technology. In its broadest definition, additive manufacturing is any layerwise construction of articles from thin layers of feed material. Additive manufacturing may involve applying liquid, layer or powder material to a workstage, then sintering, curing, melting, and/or cutting to create a layer. The process is repeated up to several thousand times to construct the desired finished component or article.

Various types of additive manufacturing are known. Examples include stereolithography (additively manufacturing objects from layers of a cured photosensitive liquid), Electron Beam Melting (using a pulverant material as feedstock and selectively melting the pulverant material using an electron beam), Laser Additive Manufacturing (using a pulverant material as a feedstock and selectively melting the pulverant material using a laser), and Laser Object Manufacturing (applying thin, solid sheets of material over a workstage and using a laser to cut away unwanted portions). Each method has advantages and disadvantages. For example, one disadvantage of Laser Additive Manufacturing is that as pulverant material is made from increasingly fine particles as required for ever-thinner layers, the pulverant material may begin to clump, and the increased surface area to volume ratio of finer particles results in higher oxidation rates.

Non-additively manufactured production parts can be traced to an original forged billet, a pour of metal at a foundry, or to the original sheet metal. It is not as easy to trace the pedigree of parts built by additive manufacturing. Economically it is unlikely that production parts will be built of a virgin material. Building five pounds of product may require one hundred pounds of powdered starting material. It is likely that the product will be built from a mixture of virgin material, previously used, recycled, or reprocessed metal powder. Powdered metals are prone to contamination through oxidation, humidity, and any remnants of a previous build. This creates a problem of documenting the condition/properties of the powdered metal used to build the end material.

SUMMARY

A method of obtaining a sample of materials includes building a product through an additive manufacturing process. A capsule is formed with an internal chamber inside of the capsule. The capsule is formed during the building of the additive manufacturing product. A sample of powder is encapsulated inside the internal chamber as the capsule is built. The internal chamber is hermetically sealed from an exterior environment to retain the sample of powder in the internal chamber.

An additional embodiment of the present invention includes a method of obtaining a sample of materials. The method includes building a product through an additive manufacturing process. A capsule is formed with an internal chamber inside of the capsule. The capsule is formed during the building of the additive manufacturing product. A sample of powder is encapsulated inside the internal chamber as the capsule is built. The internal chamber is hermetically sealed from an exterior environment to retain the sample of powder in the internal chamber. The capsule is removed from the additive engineering process after the additive manufacturing product is built. The capsule is then severed along a groove in the capsule by applying torsional stress to flanges at the distal ends of the capsule.

An additional embodiment of the present invention includes a method of obtaining a sample of materials. The method includes building a product and a capsule through an additive manufacturing process. A capsule is formed with an internal chamber inside of the capsule. A sample of powder is encapsulated inside the internal chamber as the capsule is built. Identification information of the product is provided on the capsule by the additive manufacturing process. The internal chamber is hermetically sealed from an exterior environment to retain the sample of powder in the internal chamber. The capsule is removed from the additive engineering process after the product is built. The capsule is then severed, the sample of powder is analyzed, and the analysis is used to categorize the product.

DETAILED DESCRIPTION

Figure 1:
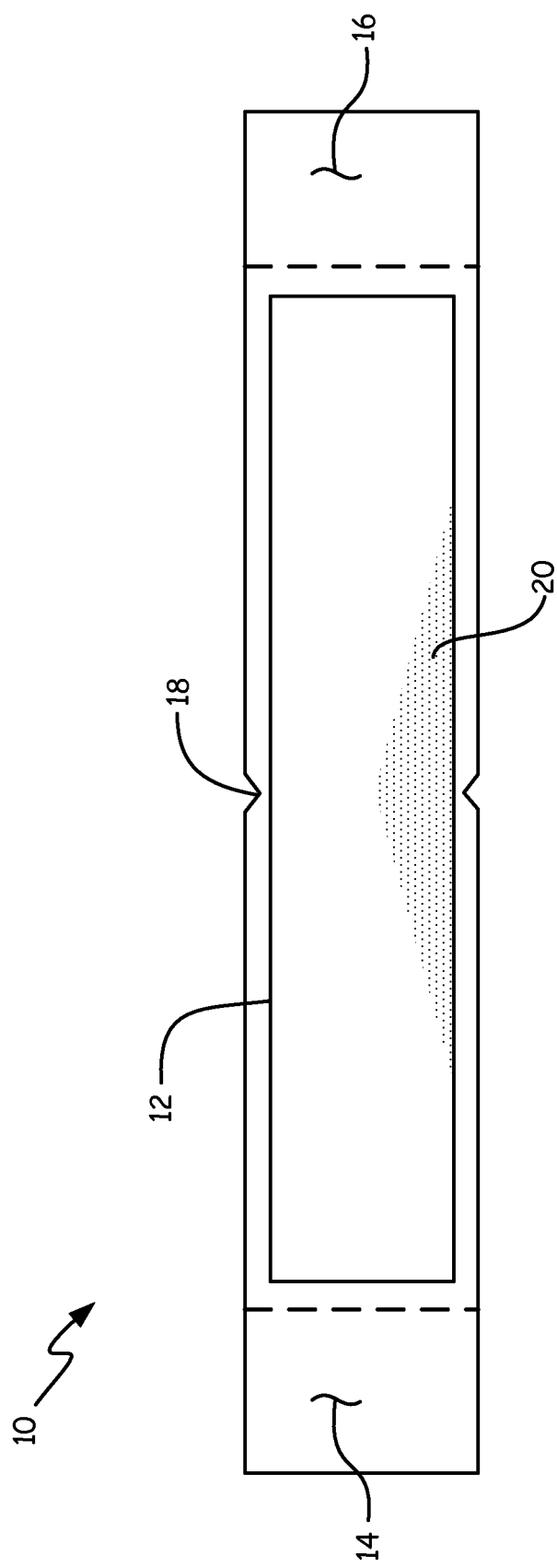
FIG. 1 is a schematic, cross-sectional view of an exemplary embodiment of a capsule in accordance with the present invention.

FIG. 1 shows a schematic, cross-sectional view of an exemplary embodiment of capsule 10 in accordance with the present invention. Capsule 10 includes internal chamber 12. First flange 14 is located at a first distal end of capsule 10. Second flange 16 is located at a second distal end of capsule 10. Groove 18 is located between first flange 14 and second flange 16 on an exterior surface of capsule 10. Groove 18 extends circumferentially around an exterior surface of capsule 10. Sample powder 20 is encapsulated within internal chamber 12 of capsule 10.

During an additive manufacturing process, capsule 10 is built concurrently with the formation of an additive manufacturing product. As the additive manufacturing product is built, capsule 10 is also built. During the formation of capsule 10, sample powder 20 is placed in internal chamber 12 of capsule 10. The encapsulation of sample powder 20 during the additive manufacturing process enables collection of the same powder used to build the additive manufacturing product.

A benefit of forming capsule 10 of sample powder 20 during the additive manufacturing process alongside the additive manufacturing product is that capsule 10 would be built, filled, and sealed during the build of the additive manufacturing product completely untouched by human hands. This method allows for minimal contamination of sample powder 20 throughout the additive manufacturing process which prevents problems associated with oxidation and humidity.

Figure 2:
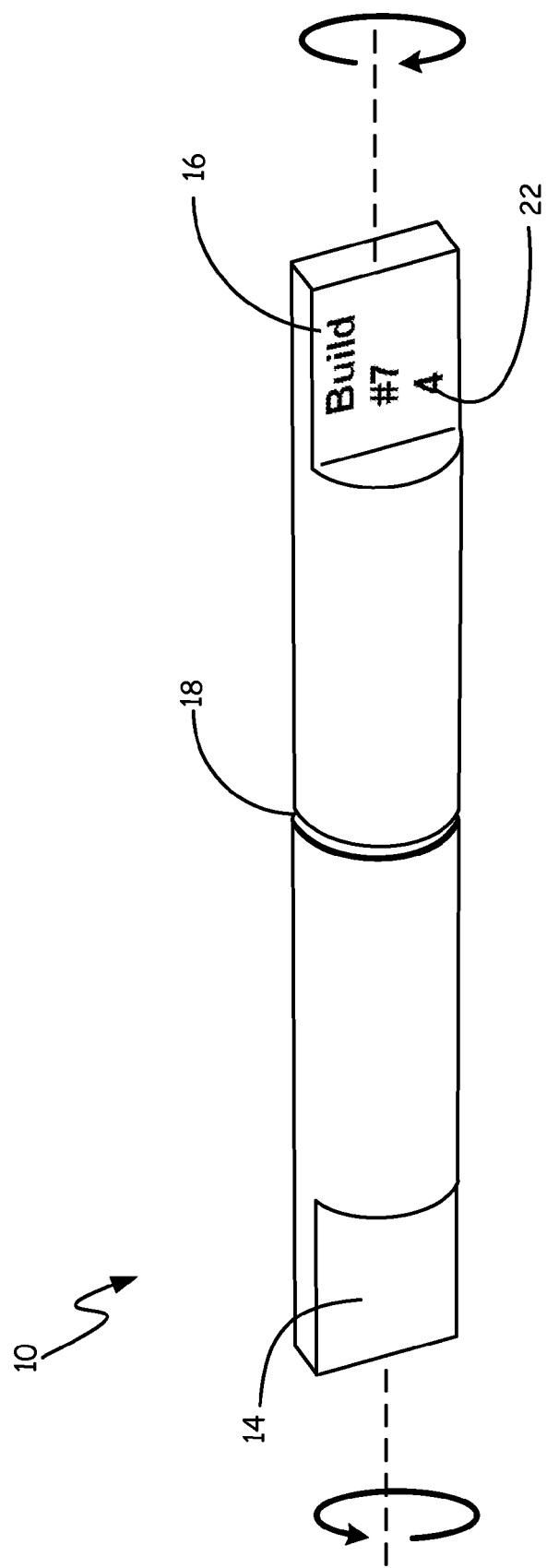
FIG. 2 is a schematic, perspective view of an exemplary embodiment of a capsule in accordance with the present invention.

FIG. 2 shows a schematic, perspective view of an exemplary embodiment of capsule 10 in accordance with the present invention. First flange 14 is located at a first distal end of capsule 10. Second flange 16 is located at a second distal end of capsule 10. Groove 18 is located between first flange 14 and second flange 16 on an exterior surface of capsule 10. Groove 18 extends circumferentially around an exterior surface of capsule 10. Identification information 22 is written onto capsule 10 during the additive manufacturing process. In this embodiment, identification information is provided on second flange 16, but can be provided anywhere on an exterior of capsule 10.

After the additive manufacturing product and capsule 10 of sample powder 20 are built, sample powder 20 can be retrieved at a later stage and analyzed to document the conditions and properties of sample powder 20. The results of analyzing the conditions and properties of sample powder 20 can then be used to classify and categorize the build conditions of the corresponding additive manufacturing product built along with sample powder 20. Sample powder 20 is retrieved from capsule 10 after severing capsule 10 by applying torsional stress to first flange 14 and second flange 16. The torsional stress causes capsule 10 to sever along groove 18 and dissects capsule 10 into two halves. Once capsule 10 has been severed, sample powder 20 is retrieved from capsule 10 to be analyzed. As opposed to traditional cutting methods involving the use of a cutting tool, severing capsule 10 with torsional stress prevents contamination of sample powder 20 that occurs when using a cutting tool.

Additionally, flanges 14 and 16 can be sectioned, polished, etched and used for metallography for evaluation of grain size, contamination, hardness, or other solid material characteristics.

Adding identification information 22 during the additive manufacturing process also decreases the risk of contamination of sample power 20. Identification information 22 is placed on capsule 10 during the additive manufacturing process instead of adding identification information 22 to capsule 10 after the build under conditions different from the controlled conditions used during the additive manufacturing process.

Figure 3:
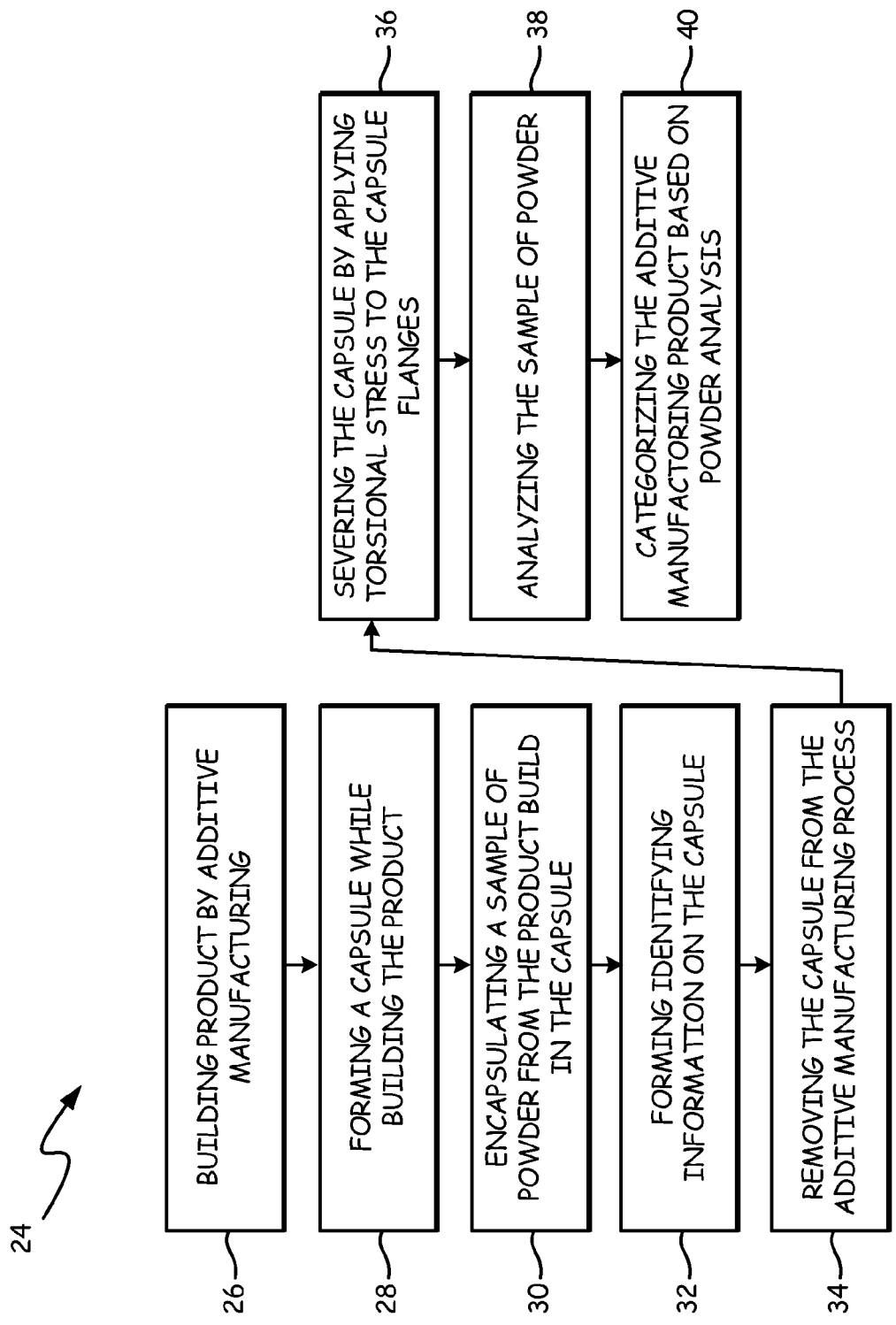
FIG. 3 is a schematic block diagram of a method incorporating the present invention.

FIG. 3 shows a schematic block diagram of method 24 of obtaining a sample of materials incorporating the present invention. Method 24 includes building a product by additive manufacturing (step 26), forming capsule 10 while building the product (step 28), encapsulating powder sample 20 from the product build in capsule 10 (step 30), forming identification information 22 on capsule 10 (step 32), removing capsule 10 from the additive manufacturing process (step 34), severing capsule 10 by applying torsional stress to first flange 14 and second flange 16 of capsule 10 (step 36), analyzing powder sample 20 (step 38), and categorizing the additive manufacturing product based on the analysis of powder sample 20 (step 40).

Building a product by additive manufacturing (step 26) includes producing a product by any additive manufacturing process that uses pulverant material for the base material. For example, Selective Laser Sintering or melting and selective Electron Beam Melting processes use pulverant granules to create an additively manufactured part. Forming capsule 10 while building the product (step 28) includes building capsule 10 at the same time as the additive manufacturing product is built. Encapsulating powder sample 20 from the product build in capsule 10 (step 30) includes forming capsule 10 to enclose powder sample 20 within capsule 10. Forming identification information 22 on capsule 10 (step 32) includes using the additive manufacturing process to produce identifying information 22 on capsule 10. During the additive manufacturing process, various language characters are created by the additive manufacturing process to form identification information 22 on capsule 10.

Removing capsule 10 from the additive manufacturing process (step 34) includes removing capsule 10 from the additive manufacturing building stage once the additive manufacturing process is complete. Severing capsule 10 by applying torsional stress to first flange 14 and second flange 16 of capsule 10 (step 36) includes twisting first flange 14 and second flange 16 of capsule 10 in opposite directions until capsule 10 severs along groove 18. After capsule 10 is severed, powder sample 20 can then be analyzed. Analyzing powder sample 20 (step 38) includes extracting powder sample 20 from the severed halves of capsule 10, and testing powder sample 20 for various characteristics including but not limited to flowability, particle size distribution, or high cycle fatigue test. Categorizing the additive manufacturing product based on the analysis of powder sample 20 (step 40) includes using the results of sample powder 20 analysis to classify and characterize the product from the corresponding additive manufacturing process.

Although the present invention has been described with reference to preferred embodiments, workers skilled in the art will recognize that changes may be made in form and detail without departing from the spirit and scope of the invention.

The invention claimed is:

1. A method of obtaining a sample, the method comprising:
   building a product with an additive manufacturing process in which the product is built layer by layer by depositing powder and selectively solidifying the powder;
   building a capsule from the powder concurrently with the product using the additive manufacturing process, wherein building the capsule includes:
   forming the capsule from the powder on a layer by layer basis to create an internal chamber;
   depositing a sample of the powder within the internal chamber as the capsule is built; and
   hermetically sealing the internal chamber so that the powder within the internal chamber is hermetically sealed from an exterior environment.

2. The method of claim 1, wherein a first flange is located at a first distal end of the capsule, and a second flange is located at a second distal end of the capsule.

3. The method of claim 2, further comprising a groove in the capsule located between the first flange and the second flange of the capsule.

4. The method of claim 3, wherein the groove extends circumferentially around an exterior surface of the capsule.

5. The method of claim 4, further comprising severing the capsule along the groove by applying torsional stress to the first flange and the second flange of the capsule.

6. The method of claim 5, further comprising analyzing the sample of powder.

7. The method of claim 6, further comprising categorizing the additive manufacturing product based on the analysis of the sample of powder.

8. The method of claim 1, wherein the powder comprises a metal powder.

9. The method of claim 1, further comprising forming identifying information on the capsule by the same additive manufacturing process used to build the capsule.

10. A method of obtaining a sample, the method comprising:
    building a product with an additive manufacturing process in which the product is built layer by layer by depositing powder and selectively solidifying the powder;

building a capsule from the powder concurrently with the product using the additive manufacturing process, wherein building the capsule includes:
  forming the capsule from the powder on a layer by layer basis to create an internal chamber;
  depositing a sample of the powder within the internal chamber as the capsule is built; and
  hermetically sealing the internal chamber so that the powder within the internal chamber is hermetically sealed from an exterior environment;
removing the capsule from the additive manufacturing process after the product is built; and
severing the capsule along a groove in the capsule by applying torsional stress to a first flange and a second flange of the capsule.

11. The method of claim 10, wherein the first flange is located at a first distal end of the capsule, and the second flange is located at a second distal end of the capsule.

12. The method of claim 11, wherein the groove is located between the first flange and the second flange of the capsule.

13. The method of claim 12, wherein the groove extends circumferentially around an exterior surface of the capsule.

14. The method of claim 10, further comprising analyzing the sample of powder.

15. The method of claim 14, further comprising categorizing the additive manufacturing product based on the analysis of the sample of powder.

16. The method of claim 10, further comprising forming identifying information on the capsule by the same additive manufacturing process used to build the capsule.

17. The method of claim 10, wherein the powder comprises a metal powder.

18. A method of obtaining a sample, the method comprising:
  building a product through an additive manufacturing process in which the product is built layer by layer by depositing metal powder and selectively solidifying the metal powder;
  building a capsule from the metal powder concurrently with the product using the additive manufacturing process, wherein building the capsule includes;
    forming an internal chamber inside of the capsule;
    depositing a sample of the metal powder within the internal chamber as the capsule is built;
    forming identifying information on the capsule using the additive manufacturing;
    hermetically sealing the internal chamber so that the metal powder within the internal chamber is hermetically sealed from an exterior environment;
  removing the product and the capsule from the additive manufacturing process after the product is built;
  severing the capsule;
  analyzing the sample of the metal powder; and
  categorizing the product based on the analysis of the sample metal powder.

19. The method of claim 18 wherein severing the capsule is along a groove in the capsule.

20. The method of claim 18 wherein severing the capsule is by applying torsional stress to a first flange at a first distal end of the capsule and a second flange at a second distal end of the capsule.

* * * * *